United States Patent [19]
Boden et al.

[11] Patent Number: 5,283,288
[45] Date of Patent: Feb. 1, 1994

[54] PVC COATINGS FOR ELECTRODES

[75] Inventors: Mark W. Boden, Millbury; Vincent A. Perciaccante, Norfolk; Stephen B. Ruiz, Boston, all of Mass.

[73] Assignee: Ciba Corning Diagnostics Corp., Medfield, Mass.

[21] Appl. No.: 817,721

[22] Filed: Jan. 7, 1992

[51] Int. Cl.$^5$ .............................................. C08L 27/22
[52] U.S. Cl. ..................................... 525/102; 525/104
[58] Field of Search ........................ 525/102, 104, 342

[56] References Cited

U.S. PATENT DOCUMENTS

| | | | |
|---|---|---|---|
| 3,850,772 | 11/1974 | Sekmakas | 204/181 |
| 4,146,585 | 3/1979 | Ward et al. | 525/104 |
| 4,341,686 | 7/1982 | Chakrabarti | 427/244 |
| 5,102,526 | 4/1992 | Brown et al. | 204/415 |

FOREIGN PATENT DOCUMENTS

| | | | |
|---|---|---|---|
| 50248 | 4/1982 | European Pat. Off. | |
| 2432006 | 2/1975 | Fed. Rep. of Germany | 525/342 |
| 2600070 | 12/1987 | France | |

OTHER PUBLICATIONS

Arkles, B., Silane Coupling Agent Chemistry, in "Silicon Compounds, Register and Review" by Petrarch Systems (1987) p. 54.

Biswas, M. et al, Recent Progress in Chemical Modification of Poly (vinyl chloride), Indian J. of Technol., 28(1990) 111.

Cheng, P. et al, Studies on the Immobilization of Bromelain on PVC Powder, Nat. Sci. Counc. Monthly, ROC, 8 (1980) 313.

Ma, S. C. et al, Response Properties of Ion-Selective Polymeric Membrane Electrodes Prepared with Animated and Carboxylated Poly (vinyl chloride), Anal. Chem., 60 (1988) 2293.

Moody, G. J. et al, Modified Poly (vinyl chloride) Matrix Membranes for Ion-selective Field Effect Transistor Sensors, Analyst 113 (1988) 1703.

Morrall, S. W. et al, Modification of Siliceous Surfaces with Alkoxysilanes from a Nonaqueous Solvent, in "Silanes, Surfaces, and Interfaces", Ed. by D. E. Leyden (1986), p. 501.

Satchwill, T. et al, Synthesis and Characterization of New Polyvinylchloride Membranes for Enhanced Adhesion on Electrode Surfaces, J. Electroanal. Chem. 2020 (1986) 75.

*Primary Examiner*—Ralph H. Dean
*Attorney, Agent, or Firm*—Arthur S. Morgenstern; Nicholas I. Slepchuk, Jr.

[57] ABSTRACT

This invention involved the discovery of novel polymers and a process for their preparation. The polymers were prepared by the nucleophilic substitution, at room temperature, of PVC with substituted alkyltrialkoxysilanes, which can be cured at room temperature to give adhesion of PVC to hydrophilic substrates. These polymers are particularly useful as adhesion promoters in ion-selective electrodes. The invention also involved the application of these adhesive primers to planar electrode substrates to give greatly improved performance in the response of ion-selective electrodes.

24 Claims, 1 Drawing Sheet

PVC COATINGS FOR ELECTRODES

BACKGROUND

The reaction of nucleophiles with polyvinylchloride (PVC) is known. (Ma, S.C. et al., Anal. Chem. 60 (1988) 2293; Chenh, P. et al, Nat'l. Sci. Council Monthly, ROC (1988) 8 (4) (1988) 313: Biswas, Mukul et al, Indian J. of Technol. 28 (1990) 111) However, it is not common to derivatize PVC for most applications due to the fragility of the polymer and the relative difficulty of the substitution reaction. Elevated temperatures can lead to dehydrochlorination, which is autocatalytic The addition of nucleophiles can also catalyze this process. The resultant polymer degradation is also accelerated by light, especially when it is in solution and at elevated temperatures. The derivatization of PVC by reaction with amines is normally carried out at high temperatures (Ma; Chenh; Biswas) and/or in a nonsolvent, such as methanol (Ma; Chenh). The result, in the first case, is a PVC which is severely degraded, and, in the second case, a polymer which is only partially derivatized. In the extreme worst case, the nucleophile is simply entrapped in the polymer matrix, giving rise to an apparent substitution reaction.

PVC is used in a number of applications in which it is desirable to have adhesion between the PVC and some substrate. Generally, the adhesion is achieved by treatment of the surface in question with a silane, such as dimethyldichlorosilane. (Harrison, D.J., J. Electroanal. Chem. 202 (1986) 75; Moody, G.J. et al, Analyst 113 (1988) 1703; Petrarch Systems, "Silicon Compounds, Register and Review" (1987) 54) In such a case, the adhesion is due to hydrophobic interactions, not the formation of covalent chemical bonds. The adhesion can be somewhat improved by the use of a silane which can form hydrogen bonds with the PVC, as these interactions are stronger than simple hydrophobic interaction.

One way to get around the fairly poor adhesion obtained by these methods is to heat the PVC extensively, in the presence of a binding agent, after it has been applied to the substrate. (Chakrabarti, S. et al, U.S. Pat. No. 4,341,686). Again, this leads to degradative dehydrochlorination of the polymer. Also, the material obtained by this method is not well-defined, nor is it necessarily crosslinked throughout the polymer layer.

One area where therefore PVC adhesion is of particular importance is in the field of ion selective electrodes (hereafter referred to as ISEs). An integral part of these electrodes are the membranes which contain the ion selective components. These membranes are most often made from highly plasticized PVC, indeed, the plasticizer content is nearly always greater than the PVC content. This fact is important, since, due to the oily nature of the plasticizers, adhesion of this membrane to any surface is extremely difficult to achieve.

Failure of the membrane to adhere to the electrode substrate can lead to shorting or shunt formation between the working electrode and the reference electrode when the entire electrode is immersed in aqueous analyte.

Another disadvantage of the highly plasticized formulations used in ISEs is their ability to flow over long periods of time. The membranes are actually a viscous liquid; storage of the electrodes can result in membranes which are not of uniform thickness. The fact that the novel polymer crosslinks upon curing prevents flow in the resulting membrane.

SUMMARY

This invention involved the discovery of novel polymers and a process for their preparation. The polymers were prepared by the nucleophilic substitution, at room temperature, of PVC with substituted alkyltrialkoxysilanes, which can be cured at room temperature to give adhesion of PVC to hydrophilic substrates. These polymers are particularly useful as adhesion promoters in ion-selective electrodes. The invention also involved the application of these adhesive primers to planar electrode substrates to give greatly improved performance in the response of ISEs.

DETAILED DESCRIPTION OF THE INVENTION

Figure 1:
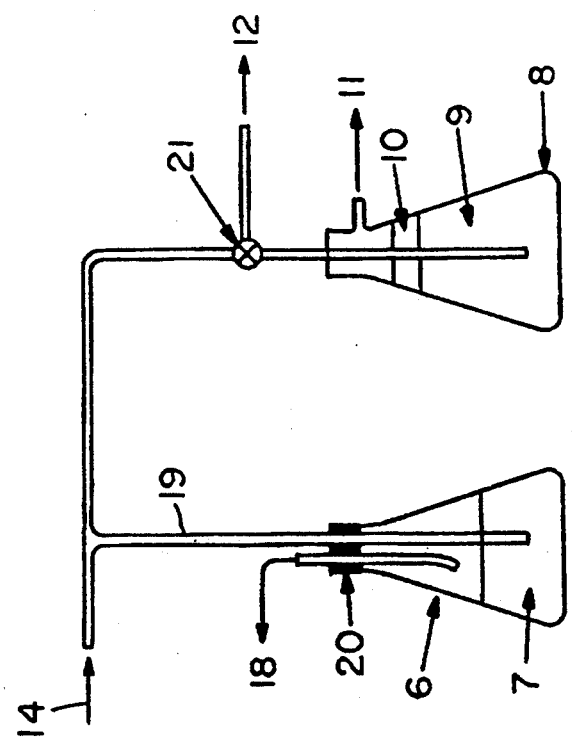
FIG. 1 shows the apparatus which is used for synthesizing the PVC copolymer coatings

This invention involved the synthesis and use of polymer coatings that chemically bond to electrodes. In the process of developing these materials, novel polymers were developed, as well as methods for preparing these polymers. In addition, novel ways of obtaining adhesive membranes for ISEs were developed.

It has long been known that silanes could be used to coat metal, glass and other surfaces that contain hydroxy groups or oxides. (Petrarch) This process, termed silanization, is used as a means of making surfaces hydrophobic and, in this case, as a means of reducing the driving force for the migration of aqueous contaminants under membranes.

By creating a polymer that would chemically adhere to the surface, a much more durable coating was made, thus extending significantly the life of electrodes The polymer that was needed was one that would not only adhere to the electrode, but also provide the matrix necessary for ion determination. Furthermore, the novel polymers were found to greatly reduce the short formation under the membrane caused by water leakage.

The polymer invented herein was a novel compound of PVC and substituted alkyltrialkoxysilane (hereafter referred to as ATAS). The current polymer was synthesized by reacting PVC with a substituted ATAS, in the presence of a polar aprotic solvent Reaction temperatures from 5 to 100 degrees C. were evaluated and found acceptable for this reaction, although a reaction temperature of room temperature (approximately 20 degrees C.) was found optimum. This reaction was found to work for any molecular weight PVC, namely molecular weights of 1,000 and high. The preferred molecular weight range was found to be 10,000-100,000, while the optimum molecular weight was found to be approximately 62,000.

In general, compounds of the structure

can be used to react with the PVC, where R1 can be an amino or mercapto group, R2 can be an alkyl or aromatic group or any organic spacer group (for example, ethers, alkenes, ketones, esters, etc.), R can be any alkyl group, including, for example, methyl, ethyl, etc., and the three R substituents do not need to be the same.

It was found that the molar ratio of PVC to ATAS in the reaction could vary from 100:1 to 1:10, with the preferred ratio being between 20:1 and 1:3. The optimum ratio was found to be approximately 5:1.

Once the reaction between PVC and ATAS occurs, compounds having the formula

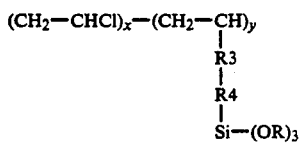

are formed. In, these copolymers, $R_3$ is a residue of either an amino or mercapto group, $R_4$ is an alkylene therefore, aromatic, or any organic spacer group, and R is any alkyl group, where the three R substituents do not need to be the same.

The copolymer has been found to perform satisfactorily when the ratio of y:x (where y and x represent the moles of monomer) varies from 1:20 to 1:500. The preferred ratio was found to be 1:100 to 1:200, while the optimum ratio was found to be approximately 1:170 (or approximately 0.6%). Alternatively, the extent of substitution for PVC can be expressed as y/(x+y), wherein satisfactory performance was found when this determinant ranged between 1/21 and 1/501, the preferred copolymer had values ranging between 1/101 and 1/201, while optimum performance was obtained when the value was approximately 1/171, The preferred aprotic solvent used in the synthesis of PVC-silane is hexamethylphosphoramide (HMPA). Examples of other suitable solvents include, but are not limited to, dimethylsulfoxide (DMSO); 1-methyl-2-pyrrolidinone; 1,3-dimethyl-3,4,5,6-tetrahydro-2(1H)-pyrimidinone; 1-methyl-2-pyrrolidinone; 1,3-dimethyl-2-imidazolidinone; N,N-dimethylformamide; and N,N-dimethylacetamide. These solvents must be scrupulously cleaned and dried in order to remove any traces of water and/or basic moieties and other impurities. The PVC is soluble in HMPA but not in DMSO. Thus, the reaction may be carried out as a one- or two-phase process.

It is desirable that the reaction take place at room temperature, to avoid degradation of the PVC. Second, the reaction is carried out under a blanket of dry, inert gas, preferably nitrogen or argon, to prevent oxidation of the polymer. Third, the system is also kept free from light to prevent photodegradation of the polymer during the reaction. Fourth, the system must be scrupulously dried to avoid premature curing of the product. The first three of these precautions have been found to prevent discoloration due to conjugated alkene formation, as all three or any combination of them catalyze dehydrochlorination in PVC.

In Chakrabarti, a PVC and substituted ATAS were mixed at the point of application, then heated to 80 degrees C. to provide an adhesive for attaching cover layers of cellular and non-cellular polyurethane layers. The product was not isolated or identified. The instant polymer is an isolated and distinct chemical species of known composition. The method of adhesion in Chakrabarti depends on the migration of the silane to the surface of the polymer, where it is cured at elevated temperatures. One advantage of the instant polymer is that the siloxane groups are dispersed throughout the polymer film. This gives rise to a uniformly crosslinked system upon curing, giving strength through the whole polymer layer, rather than just at the surface. In addition, the instant polymer is much more flexible, giving the possibility of application under a variety of conditions, and room temperature curing. This property is particularly important for use in ISEs, since the electrochemistry is very sensitive to the polymer matrix; only minimal variation from the parent PVC can be made without significantly affecting performance.

In using the novel polymers to coat substrates, between 0.1 and 10% by weight solutions of the substituted PVC in volatile solvents, for example anhydrous tetrahydrofuran, are prepared. Optimum concentration was approximately 1% by weight. The substrates were coated to give layers of from 0.1 to 10 microns thick, preferably 1 micron in thickness. Cure times varied from 2 to 24 hours, depending upon the curing temperature, which could range from below room temperature (as low as approximately 0° C.) up to approximately 100° C. The preferred temperature for curing was room temperature. Adhesion was improved by soaking the coated substrate in water for 5 minutes prior to curing.

Analysis of variations of the instant polymer showed that, with the optimal-performing polymer, 0.5–0.6% of the chlorines of the PVC was reacted with the silane. Somewhat less preferred, but still very good, performance was found for substitution ranging from 0.15–4.5%. Other percent substitutions, from 0.05% up to the point where the polymer fails to behave as PVC (which is determined by the particular application), have also been found to perform satisfactorily. The reaction of PVC with ATAS releases, as a by-product, both hydrogen and chloride ions. It is useful to add a proton scavenger to the system, to remove the hydrogen which is released (along with the chlorine) when the PVC reacts with the ATAS. The amount of proton scavenger needed is dependent on the amount of substitution which is obtained Ratios of moles of scavenger to moles of total chlorine in PVC starting material have been investigated, and acceptable performance has been found when the ratios range between 1:100 and 10:1. Preferred ratios have been found to range between 1:20 and 10:1. Optimum performance has been found when the ratio is approximately 1:10.

The reaction by-product, hydrochloric acid (HCl), may be removed by reaction with hindered bases such as 2,6-di-tert- butylpyridine, diazabicyclo compounds, such as 1,4-diazabicyclo[2.2.2]octane, 1,5-diazabicyclo[4.3.0]non-5-ene,.: 1,8-diazabicyclo[5.4.0]undec-7-ene, or by tertiary amines such as tridodecylamine; N,N-diisopropylethylamine or di-tert-butylethylamine. In addition, the HCl may be removed by reaction with the excess substituted ATAS, since there is a large excess of this compound in the reaction.

The instant polymers and processes are useful primarily as adhesion promoters in ion selective and planar electrodes. It should be emphasized that the instant coating techniques are primarily useful for electrodes made of glass or aluminum or other metals/metal oxides However, they are also usable on any materials that have hydroxyl or other groups that can react with the substituted ATAS.

The polymer materials and techniques disclosed herein also have applicability in various other areas. For example, the materials and processes have applicability in the adhesive area.

The following examples describe various aspects of the synthesis and use of the novel polymers described herein, but are not intended to limit the usefulness of the newly invented materials or processes.

EXAMPLE 1

Figure 2:
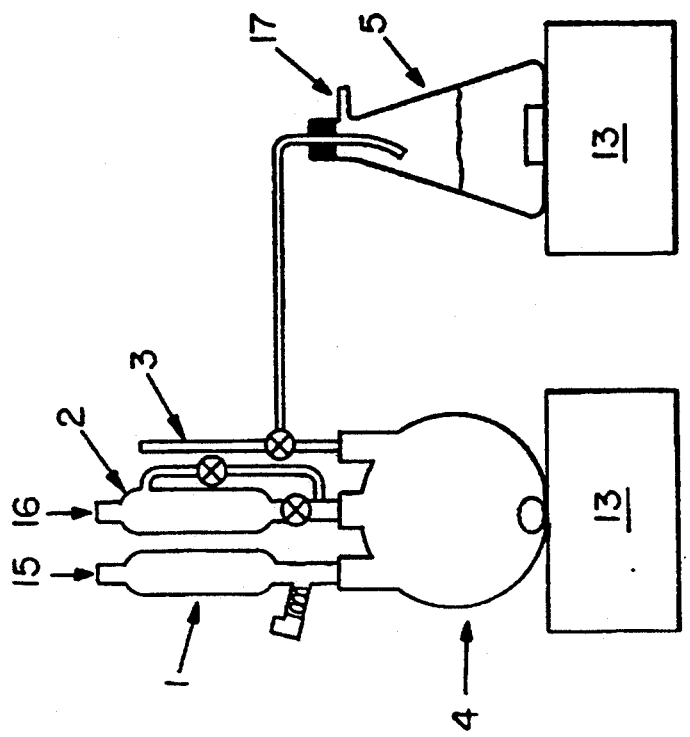
FIG. 2 represents constant pressure apparatus, which is used to maintain an inert atmosphere at 1 atmosphere pressure for use in the reaction.

The apparatus used to synthesize the PVC copolymer coatings is shown in FIG. 1. 1 is a powder addition funnel. 2 is a pressure equalizing addition funnel. 3 is a sampling and draw-off tube with a 3-way stopcock. 4 is a 3-neck roundbottom flask. 5 is a side-arm Erlenmeyer flask containing precipitation solvent. 13 represent stirrers FIG. 2 represents the constant pressure apparatus, which is used to produce an inert atmosphere at 1 atmosphere pressure for use in the reaction. 6 is an Erlenmeyer flask with a 2-hole rubber stopper (20), having a mercury resevoir (7). One opening is connected to the atmosphere (18), while the other (19) is connected to the rest of the system. 8 is a side-arm flask, containing potassium hydroxide pellets (9), covered with glass wool (10). The side arm is connected to a vacuum line 11, while the outlet of this flask is connected via a three-way stopcock (21) to either the balance of the system or an inert gas (12). To obtain a constant pressure, inert gas environment, the constant pressure system is introduced to vacuum through line 11 to remove all gases from the system. Line 11 is then sealed and line 12 opened to introduce argon (or another inert gas) to the system until the pressure is again at equilibrium with the atmosphere. This procedure is repeated two additional times to insure removal of all oxygen from the system. The outlet 14 is then connected to the appropriate inlet to the reaction system (15, 16, or 17) without opening the system to the atmosphere.

All glassware used in the reaction is coated with black plastic to exclude light during the reaction. The reaction is maintained under a blanket of argon (or other inert gas) at atmospheric pressure. Initially, the system is set up with a measured amount of PVC in the powder funnel and a measured amount of the substituted ATAS in the addition funnel. A proton scavenger can be added to the addition funnel as well. The solvent for the reaction is present in the desired amount in the round bottom flask.

The solvent is purified to remove amines. It is refluxed in the presence of 4-nitrophenyl hippuric acid ester for 24 hours. The mixture is cooled and pure solvent isolated by distillation in vacuo. The distillate is stirred at 50° C. over barium oxide, in an atmosphere of dry nitrogen, for 24 hours. The solvent is isolated by distillation in vacuo, and the process is repeated to give clean, dry solvent for the reaction.

Polyvinylchloride, (5 gm, 0.08 mol) is added slowly and with rapid stirring to 100 ml of HMPA. The HMPA has been previously exhaustively purified as described above. The solution is stirred for 24 hours (a previously determined amount of time) at room temperature to insure that all PVC is dissolved in the solvent. After this time, aminopropyltriethoxysilane, (3.6 gm, 0.016 mol) is added to the rapidly stirred reaction dropwise. The solution is stirred under these conditions for 48 hours. It is purified by addition, still under the inert atmosphere, to 2 liters of dried and distilled methanol. The solid polymer is filtered off, under an inert atmosphere, then redissolved into scrupulously dried tetrahydrofuran and precipitated into hexane. Note that the polymer continues to be kept under an inert atmosphere. The filtration, dissolution, and precipitation into hexane is repeated once more. The process yields approximately 80% of the theoretical amount of the product, with a substitution (i.e. ratio of silicon to chlorine) of 0.6%. It should be stressed that any introduction of water at any stage in this process will lead to premature curing of the polymer, rendering it insoluble and useless for further processes.

EXAMPLE 2

A process similar to that used in Example 1 was used, except that other polar aprotic solvents were substituted for the HMPA. The solvents used were 1-methyl-2-pyrrolidinone; 1,3-dimethyl-3,4,5,6,-tetrahydro-2(1H)-pyrimidinone; 1,3-dimethyl-2-imidazolidinone; N,N-dimethylformamide, and dimethylsulfoxide. The results were as follows:

| Solvent | % substitution |
|---|---|
| hexamethylphosphoramide | 0.60–0.79 |
| 1,3-dimethyl-2-imidazolidinone | 0.78 |
| 1,3-dimethyl-3,4,5,6-tetrahydro-2(1H)-pyrimidinone | 1.5 |
| dimethylsulfoxide | 0.17 |
| 1-methyl-2-pyrrolidinone | 4.5 |

EXAMPLE 3

A process similar to that used in Example 1 was used, except that different silanes were substituted for aminopropyltriethoxy silane. The silanes used were aminopropyltrimethoxy silane and mercaptopropyltriethoxy silane.

EXAMPLE 4

A process similar to that used in Example 1 was used, except that proton scavengers were added. The following proton scavengers were used: 2,6-di-t-butylpyridine, 1,4-diazabicyclo[2.2.2]octane, 1,5-diazabicyclo[4.3.0]non-5-ene, 1,8-diazabicyclo[5.4.0]undec-7ene, tridodecylamine, N,N-diisopropylethylamine or di-tert-butylethylamine.

It should be noted that the addition of these scavengers is particularly important in reactions involving mercaptosilanes The scavengers served to remove HCl, which could cause dehydrochlorination.

EXAMPLE 5

A process similar to that used in Example 1 was used except that differing amounts of substituted ATAS were used. The results are shown below.

| Moles ATAS | Moles PVC | Reaction Time (min.) | Substitution |
|---|---|---|---|
| 1 | 1 | 24 | 0.63 |
| 0.2 | 1 | 48 | 0.60 |
| 3 | 1 | 24 | 1.5 |

EXAMPLE 6

The novel polymers described above were analyzed using the following techniques. Percent substitution was determined by elemental analysis, using the ratio of nitrogen and/or silicon to chlorine found in the product. The thoroughness of the removal of solvent was also determined by elemental analysis, using the ratio of silicon to nitrogen, with complete removal being achieved when the ratio is 1:1. FTIR analysis was also used to confirm complete removal of solvent. Results of typical analyses are shown below.

| Elemental Analysis | |
|---|---|
| Element | Percent Found |
| Carbon | 38.84 |
| Hydrogen | 4.91 |
| Nitrogen | 0.12 |
| Chlorine | 53.45 |
| Silicon | 0.24 |

EXAMPLE 7

The application method used to coat planar substrates with the substituted PVC is as follows: The substituted PVC is dissolved in anhydrous tetrahydrofuran to give a 1% by weight solution. To minimize water contamination and premature polymer reaction, the solution is mixed in a dry glove box and stored in a presilanized bottle with a septum cap. The substrate is cleaned prior to coating with techniques suitable for removing surface particulates and organic contamination (grease). The preferred method used was a water rinse, N2 purge to dry, and plasma etching (3 min. Oxygen and 5 min. Argon cycle used at 300 watts). Upon removal from the plasma etcher, the substrates were spin coated with the substituted PVC solution to give a layer approximately 1 micron thick. The cure is affected at room temperature at high humidity over a 24-hour period.

EXAMPLE 8

An application method similar to that used in Example 7 except that the coated substrates were cured at 80° C. for 2 hours. The shorter cure time was at the expense of increased degradation of PVC.

EXAMPLE 9

An application method similar to that used in Example 7 and Example 8 except that non-planar substrates are coated using techniques suitable for their geometries, such as, dip coating and spray coating.

What is claimed is:

1. A composition consisting of a copolymer of polyvinylchloride and substituted alkyltrialkoxysilane of the formula

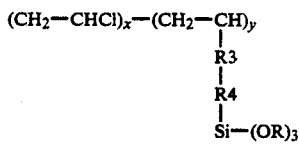

where R3 is either a residue of an amino or mercapto group, R4 is an alkylene, aromatic, or any other organic group, R is an alkyl group, where the three R substituents do not need to be the same, and where x and y represent moles of monomer incorporated in the polymer and x / y represents the mole ratio of

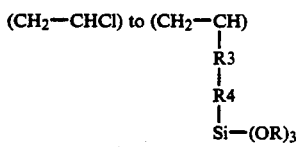

in the copolymer.

2. The composition of claim 1 wherein the molecular weight of the polyvinylchloride starting material is greater than 1,000.
3. The composition of claim 1 wherein y/(x+y) is between 1/21 and 1/501.
4. The composition of claim 3 wherein y/(x+y) is between 1/101 and 1/201.
5. The composition of claim 4 wherein y/(x+y) is approximately 1/171.
6. A process for making a composition of claim 1 comprising reacting polyvinylchloride and substituted alkyltrialkoxysilane in the presence of a polar aprotic solvent, followed by isolation and purification of said copolymer.
7. A process of claim 6 wherein the ratio of the moles of chlorine in the polyvinylchloride to the moles of substituted alkyltrialkoxysilane in the reaction mixture is between 100:1 and 1:10.
8. A process of claim 7 wherein the ration of the moles of chlorine in the polyvinylchloride to the moles of substituted alkyltrialkoxysilane in the reaction mixture is between 20:1 and 13.
9. A process of claim 8 wherein the ratio of the moles of chlorine in the polyvinylchloride to the moles of substituted alkyltrialkoxysilane in the reaction mixture is approximately 5:1.
10. A process of claim 6 in which the reaction is conducted between 5 and 50 degrees C.
11. A process of claim 11 in which the reaction is
12. A process of claim 6 wherein the aprotic solvent is selected from the group consisting of hexamethylphosphoramide; dimethylsulfoxide; 1-methyl-2-pyrrolidinone; 1,3-dimethyl-3,4,5,6,-tetrahydro-2(iH)-pyrimidinone; 1-methyl-2-pyrrolidinone; 1,3-dimethyl-2-imidazolidinone; N,N-dimethylformamide; and N,N-dimethylacetamide.
13. A process of claim 12 wherein the aprotic solvent is hexamethylphosphoramide.
14. A process of claim 6 which is conducted in a two-phase system.
15. A process of claim 6 which is conducted in a one-phase system.
16. A process of claim 6 in which the reaction is conducted in an environment comprising a dry, inert gas.
17. A process of claim 16 in which the inert gas is argon or nitrogen.
18. A process of claim 6 in which the reaction is conducted in the dark.
19. A process of claim 6 which is conducted in the presence of a proton scavenger or to which a proton scavenger is added after the reaction is begun.
20. A process of claim 19 wherein the proton scavenger is selected from hindered bases, diazobicyclo compounds and excess substituted alkyltrialkoxysilane.
21. A process of claim 20 wherein the proton scavenger is selected from the group consisting of 2,6-di-tert-butylpyridine; 1,4-diazabicyclo[2.2.2]octane; 1,5-diazabicyclo[4 . 3 . 0 non-5-ene; 1,8-diazabicyclo[5.4.-0]undec-7-ene; tridodecylamine; N,N-diisopropylethylamine and di-tert-butylethylamine.
22. A process of claim 19 wherein the ration of moles of proton scavenger to moles of chlorine in the starting material ranges from 1:100 to 10:1.
23. A process of claim 22 in which the ratio is between 1:20 and 10:1.
24. A process of claim 23 in which the ratio is approximately 1:10.

* * * * *

UNITED STATES PATENT AND TRADEMARK OFFICE
CERTIFICATE OF CORRECTION

PATENT NO. : 5,283,288
DATED : February 1, 1994
INVENTOR(S) : Boden et al.

It is certified that error appears in the above-identified patent and that said Letters Patent is hereby corrected as shown below:

Column 8, line 29, delete "A process of claim 11 in which the reaction is" and insert therefore --A process of claim 10 wherein the ratio of the moles of chlorine in the polyvinylchloride to the moles of substituted alkyltrialkoxysilane in the reaction mixture is between 20:1 and 1:3.--

Signed and Sealed this

Thirteenth Day of July, 1999

Attest:

Q. TODD DICKINSON

Attesting Officer

Acting Commissioner of Patents and Trademarks